United States Patent [19]

Takhashi

[11] Patent Number: 4,704,018
[45] Date of Patent: Nov. 3, 1987

[54] EYE FUNDUS OBSERVING AND PHOTOGRAPHING APPARATUS

[75] Inventor: Fumio Takhashi, Tonemachi, Japan

[73] Assignee: Nippon Kogaku K.K., Tokyo, Japan

[21] Appl. No.: 782,103

[22] Filed: Sep. 30, 1985

[30] Foreign Application Priority Data

Oct. 4, 1984 [JP] Japan ................. 59-208788

[51] Int. Cl.$^4$ ................................. A61B 3/14
[52] U.S. Cl. ..................... 351/206; 354/62
[58] Field of Search ............ 351/206, 207; 354/62

Primary Examiner—Rodney B. Bovernick
Assistant Examiner—D. M. Dzierzynski
Attorney, Agent, or Firm—Shapiro and Shapiro

[57] ABSTRACT

An eye fundus observing and photographing apparatus has an illuminating optical system for supplying illuminating light to an eye to be examined, an optical system for observing and photographing the fundus of the eye to be examined through an observation aperture stop, and an objective lens common to the illuminating system and the observing and photographing system. The objective lens is comprised of a first component which is a cemented positive meniscus lens having its concave surface facing the eye to be examined and a second component which is a cemented positive meniscus lens having its concave surface facing the observation aperture stop. The center of curvature of the concave surface of the first component which is adjacent to the eye to be examined is coincident with a position conjugate with the observation aperture stop with respect to the entire objective lens. The center of curvature of the concave surface of the second component which is adjacent to the observation aperture stop is coincident with the position of the observation aperture stop. A position conjugate with the observation aperture stop with respect to the reflected illuminating light on the cemented surface of the first component and a position conjugate with the observation aperture stop with respect to the reflected light of the illuminating cemented surface of the second component are substantially coincident with each other. The magnifications of the images of the observation aperture stop by the reflection on the cemented surfaces of the two components are substantially coincident with each other.

12 Claims, 2 Drawing Figures

EYE FUNDUS OBSERVING AND PHOTOGRAPHING APPARATUS

BACKGROUND OF THE INVENTION

1. Field of the Invention

This invention relates to an apparatus for observing or photographing the fundus of an eye, and in particular to improvements in an optical system including an objective lens common to the illuminating system and the observing and photographing system thereof.

2. Description of the Prior Art

In an eye fundus observing and photographing apparatus of the type in which an objective lens is common to the illuminating optical system and the observation optical system, if the illuminating light reflected by the objective lens mixes in the observing and photographing system, the quality of the image of the fundus of an eye by the observing and photographing system will be remarkably deteriorated. Therefore, various contrivances have heretofore been made for the light reflected by the objective lens. In recent years, various objective lenses comprised of two or more lens groups have been proposed to meet the desire to make the photographing angle of view wider. If the number of lenses and the number of component groups are increased, the refractive power of the objective lens can be diffused and therefore the angle of view can be made wider, but the elimination of the ghost light by the reflection on the lens surface becomes difficult.

As an idea for solving such a problem, for example, an objective lens comprising two positive meniscus lenses disposed with their convex surfaces facing each other is disclosed in German Utility Model Publication No. 1694082. Here, the cornea of the eye to be examined and the observation aperture on the examiner side are in conjugate relation with the entire objective lens, the positive meniscus lens adjacent to the eye to be examined has its concave surface facing the eye to be examined, the center of curvature thereof is coincident with a position conjugate with the observation aperture with respect to the entire objective lens, the positive meniscus lens adjacent to the observation aperture side has its concave surface facing the observation aperture side and the center of curvature thereof is coincident with the observation aperture. An example in which one or both of the two positive meniscus lenses are constructed as a cemented lens is also shown in said German utility model publication. In this objective lens, however, the lens surfaces on which the elimination of the reflected light is taken into consideration are only the lens surface which is adjacent to the eye to be examined and the lens surface which is adjacent to the observation aperture. With regard to the convex surfaces facing each other, said German utility model publication mentions that anti-reflection films are provided thereon, but discloses no means for eliminating the reflected light, including the cemented surface of each lens. The reflectance of the retina of the eye fundus is as low as several percent and an intense strobo is used for the photographing thereof and therefore, the reflected light even on the lens surfaces provided with anti-reflection films or the cemented surfaces cannot be neglected but reduces the quality of the image and thus, the objective lens disclosed in the aforementioned German utility model publication has lacked practical utility.

An example of an objective lens comprising two positive meniscus lenses having their convex surfaces facing each other is shown also in U.S. Pat. No. 3,914,032. In this objective lens, the constructions of the concave surface adjacent to the eye to be examined and the concave surface adjacent to the observation aperture are the same as those in the aforementioned German utility model publication, but this U.S. patent further shows a construction in which the light reflected by the cemented surface provided in the positive meniscus lens adjacent to the eye to be examined is eliminated with the light reflected by the convex surface of this positive meniscus lens. That is, in this patent, there is disclosed a construction in which, of the refracting surfaces other than the first and last surfaces of the objective lens as counted from the eye to be examined, the radius of curvature of that surface having its center of curvature on the eye to be examined side is 80% or less of the combined focal length of the objective lens and in order to eliminate the light reflected by the opposed surfaces of the two positive meniscus lenses and the cemented surface provided in the lens adjacent to the eye to be examined, a light-intercepting material is provided on the vertex of the lens surface of each lens which is adjacent to the observation aperture.

Here, the condition under which the radius of curvature of that refracting surface having its center of curvature on the eye to be examined side is 80% or less of the combined focal length of the objective lens has been a condition necessary to reduce the size of the image of the observation aperture by the reflected light on this surface and to eliminate the light reflected by the light-intercepting material provided on the lens surface. However, limiting the radius of curvature to a small value by such a condition, not only tends to make the distribution of refractive power onto this surface excessively great and adversely affect the aberration correction, but also makes it difficult to secure the effective diameter of the lens and thus has been disadvantageous to making the angle of view wider.

SUMMARY OF THE INVENTION

It is an object of the present invention to provide an eye fundus observing and photographing apparatus which is of a wide angle of view and good in imaging performance and moreover capable of sufficiently eliminating the harmful reflected light on the lens surface and obtaining a clear eye fundus image.

The basic technical idea of the present invention resides in constructing an objective lens common to an illuminating system and an observing and photographing system by two cemented positive meniscus lens components having their convex surfaces facing each other, making the positions conjugate with an observation aperture stop with respect to the reflected illuminating light created on the cemented surfaces of these two components substantially coincident with each other, and making the magnifications of the illuminating light created on the cemented surfaces of the two components substantially coincident with each other. By such a construction, it is possible to make the light-intercepting materials in the illuminating system which are necessary to eliminate the light reflected from the cemented surfaces smaller, reduce the undesirable possibility of the images of the light-intercepting materials proving a hindrance during observation and photographing and at the same time, increase the degree of freedom of designing of the lens system by the cemented surfaces and further improve the imaging performance.

Specifically, the construction of the present invention comprises in an eye fundus observing and photographing apparatus having an illuminating optical system for supplying an illuminating light to eye to be examined, an optical system for observing and photographing the fundus of the eye to be examined through an observation aperture stop, and an objective lens common to said illuminating system and said observing and photographing system, said objective lens being comprised of a first component which is a cemented positive meniscus lens having its concave surface facing the eye to be examined and a second component which is a cemented positive meniscus lens having its concave surface facing the observation aperture stop, the center of curvature of the concave surface of the first component which is adjacent to the eye to be examined being coincident with a position conjugate with the observation aperture stop with respect to the entire objective lens, the center of curvature of the concave surface of the second component which is adjacent to the observation aperture stop being coincident with the position of the observation aperture stop, a position conjugate with the observation aperture stop with respect to the reflected illuminating light on the cemented surface of the first component and a position conjugate with the observation aperture stop with respect to the reflected illuminating light on the cemented surface of the second component being substantially with each other, and the magnifications of the images of the observation aperture stop by the reflection on the cemented surfaces of said two components being substantially coincident with each other.

More specifically, both of the first and second components comprise a biconcave negative lens and a biconvex positive lens cemented together, and in order to eliminate the reflected light on the cemented surface of each component, the image of a common light-intercepting material is projected from the illuminating system, and in order to eliminate the reflected light on the opposed convex surfaces of the two components, the images of two further light-intercepting materials are projected.

DESCRIPTION OF THE PREFERRED EMBODIMENT

Figure 1:
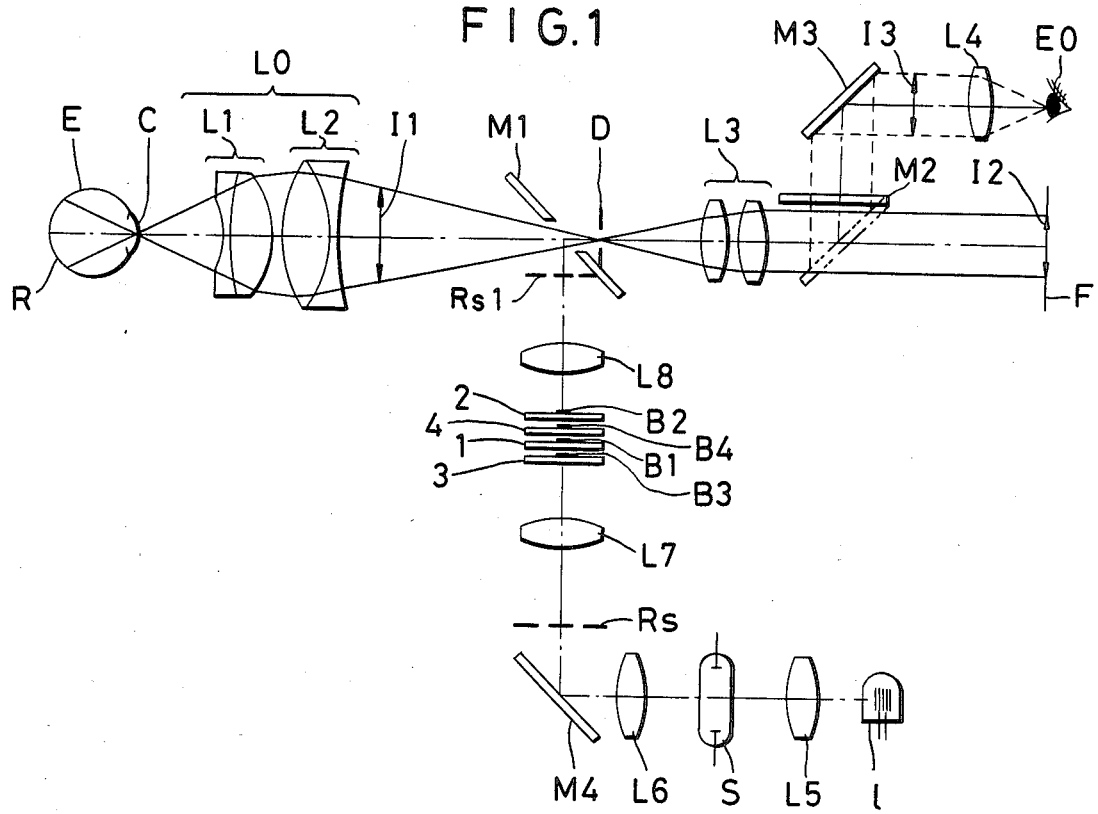
FIG. 1 is a schematic optical path diagram showing the optical system of an embodiment of the eye fundus observing and photographing apparatus according to the present invention.

FIG. 1 is a schematic optical path diagram showing the construction of the optical system of an embodiment of the eye fundus observing and photographing apparatus according to the present invention. An objective lens $L_0$ is comprised of a first component $L_1$ comprising a cemented positive meniscus lens consisting of a biconcave negative lens and a biconvex positive lens cemented together, and a second component $L_2$ comprising a cemented positive meniscus lens consisting of a biconcave negative lens and a biconvex positive lens cemented together, the first and second components $L_1$ and $L_2$ being disposed with their convex surfaces facing each other. The objective lens forms a primary image $I_1$ of the fundus R of an eye E to be examined. This primary image $I_1$ is re-imaged by a relay lens $L_3$ through an apertured reflecting mirror $M_1$ and an observation aperture stop D to form a secondary image $I_2$ of the fundus of the eye on a film surface F. A pivotally movable mirror $M_2$ is disposed between the relay lens $L_3$ and the film surface F and, when this mirror $M_2$ is obliquely disposed at a position as indicated by the dotted line, a secondary image of the fundus of the eye is formed at the focus position of an eyepiece $L_4$ by a light beam reflected by the mirror $M_2$, through an optical path bending mirror $M_3$, and the fundus of the eye to be examined may be observed by the examiner's eye $E_o$ through the eyepiece.

An illuminating light source 1 is disposed at a position substantially conjugate with a strobo S with respect to a condensing lens $L_5$. The illuminating light beam from these illuminates the opening portion of a ring slit Rs through a condenser lens $L_6$ and an optical path bending mirror $M_4$. The shape of the ring slit Rs is disclosed in U.S. Pat. No. 4,322,137. The light beam passed through the opening portion of the ring slit Rs is imaged at a position Rsl near the obliquely disposed apertured reflecting mirror $M_1$ and conjugate with the ring slit Rs by relay lenses $L_7$ and $L_8$. Illuminating light is supplied to the fundus R of the eye by a ring slit image deflected by the apertured reflecting mirror $M_1$ and re-imaged on the cornea C of the eye E to be examined through the objective lens $L_0$.

Figure 2:
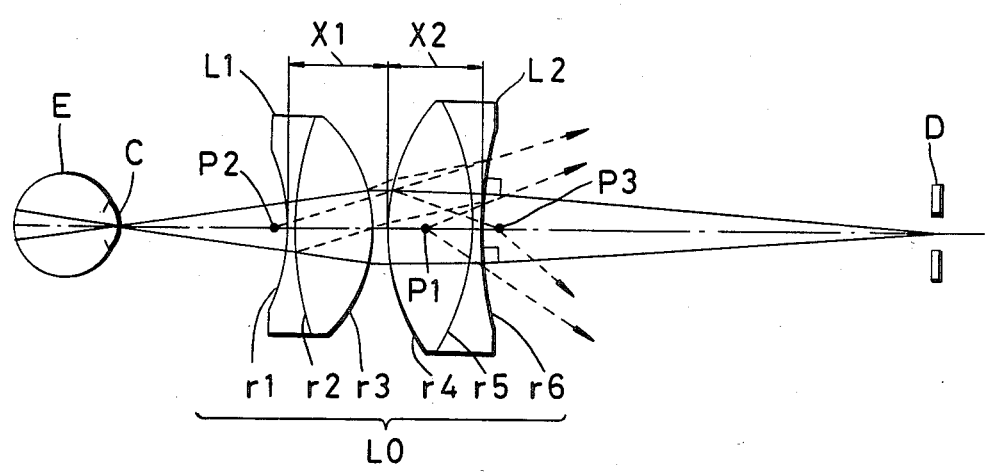
FIG. 2 is an optical path diagram showing an objective lens in this embodiment and the positions of black point images.

First to fourth light-intercepting materials $B_1$, $B_2$, $B_3$ and $B_4$ are provided on black point plates 1, 2, 3 and 4, respectively, disposed between the relay lenses $L_7$ and $L_8$ in the illuminating optical system, and black point images for eliminating harmful reflected light projected onto the interior and vicinity of the objective lens $L_0$ and created on each lens surface of the objective lens are formed by the relay lens $L_8$. The use of black point plates in an eye fundus observing and photographing optical system like the present invention is disclosed in U.S. Pat. No. 4,322,137. FIG. 2 is an optical path diagram showing the manner in which the light ray emitted from the observation aperture stop D is reflected by each lens surface of the objective lens $L_0$ and exits toward the observation opening side, in order to explain the positional relation between the images of the light-intercepting materials, i.e., the black point images, for eliminating the reflected light on each lens surface of the objective lens. In FIG. 2, solid lines indicate the conjugate relation between the observation aperture stop D and the cornea C of the eye to be examined and dotted lines indicate the optical paths of the reflected lights on the respective lens surfaces. Assuming that, as shown in FIG. 2, the lens surfaces of the lenses constituting the objective lens $L_0$ are $r_1$–$r_6$ in succession from the eye to be examined, the center of curvature of the lens surface $r_1$ which is most adjacent to the eye to be examined is coincident with the cornea C of the eye to be examined and the center of curvature of the lens surface $r_6$ which is most adjacent to the observation aperture stop is coincident with the observation aperture stop D. Thus, the image of the observation aperture stop by the reflected light on the lens surface $r_1$ which is most adjacent to the eye to be examined is at one-to-one magnification and in conjugate relation as the real image with the observation aperture stop. Further, by making the lens surface non-spherical and correcting the spherical aberration in this conjugate relation, the reflection on the lens surface $r_1$ can be dealt with equivalently to that on the lens surface $r_6$ which is most adjacent to the observation aperture stop. By making the inner diameter of the ring slit image Rsl larger than the observation aperture stop D, it is possible to eliminate the harmful light rays reflected by the refracting surface of the objective lens and mixing in the observation aperture stop D. Here, the observation aperture stop D and the cornea C of the eye to be examined are disposed conjugately with each other with respect to the entire objective lens $L_0$ and, in order that these may be imaged without spherical aberration, a non-spherical surface is provided on the most effective fourth surface $r_4$, i.e., the convex surface of the second component $L_2$ which is adjacent to the eye to be examined.

The lens $L_0$ is constructed so that the position conjugate with the observation aperture stop with respect to the reflection by the cemented surfaces $r_2$ and $r_5$ of the first and second components is substantially coincident with a point $P_1$ in FIG. 2 and the reflection magnifications of the surfaces $r_2$ and $r_5$ are equal to each other so that the reflected illuminating light on the surfaces $r_2$ and $r_5$ does not pass through the observation aperture stop D, and a first black point image is projected onto this point $P_1$. Here, with respect to the reflected illuminating light on the surface $r_2$, the point $P_1$ corresponds to the real image of the stop D, and with respect to the reflected illuminating light on the surface $r_5$, the point $P_1$ corresponds to the virtual image of the stop D. This first black point image is formed by the first light-intercepting material $B_1$ disposed between the relay lenses $L_7$ and $L_8$ in the illuminating optical system being projected into the objective lens by the relay lens $L_8$. The size of the first light-intercepting material $B_1$ is determined so that on the basis of the magnification of the image of the observation aperture stop by the reflected light on each cemented surface $r_2$, $r_5$ and the projection magnification of the first light-intercepting material $B_1$, the size of the first black point image can cover the image of the observation aperture stop at the point $P_1$.

Also, there is an undesirable possibility that the reflected light on the third surface $r_3$ of the first component $L_1$, of the surfaces of the first and second components $L_1$ and $L_2$ which face each other, may pass through the fourth, fifth and sixth surfaces $r_4$, $r_5$, $r_6$ and exit from the objective lens and then pass through the observation aperture stop, but by projecting a second black point image onto a position $P_2$ conjugate with the observation aperture stop with respect to the reflection on the third surface $r_3$, the reflected light on this surface is eliminated. The point $P_2$ corresponds to the virtual image of the stop D with respect to the reflected illuminating light on the surface $r_3$. In order to eliminate the reflected light on the convex surface $r_4$ of the second component $L_2$, a third black point image is likewise projected onto a position $P_3$ conjugate with the observation aperture stop with respect to the reflection on this surface. The point $P_3$ corresponds to the real image of the stop D with respect to the reflected illuminating light on the surface $r_4$. These second and third black point images are formed by the second and third light-intercepting materials $B_2$ and $B_3$ provided on the second and third black point plates 2 and 3, respectively, disposed between the relay lenses $L_7$ and $L_8$ in the aforementioned illuminating optical system being projected onto the objective lens by the relay lens $L_8$. The sizes of the second and third light-intercepting materials $B_2$ and $B_3$ are determined so that on the basis of the magnifications of the images of the observation aperture stop by the reflected light on the refracting surfaces $r_3$ and $r_4$ and the projection magnifications of the respective light-intercepting materials, the size of each black point image can cover the image of the observation aperture stop with respect to the reflection on each refracting surface.

Now, it is desirable that the positions of the black point images as described above satisfy the following conditions:

$$-\frac{2(X_1 + X_2)}{5} < P_1 < -\frac{X_1 + X_2}{5} \quad (1)$$

$$-\left(\frac{3X_1}{2} + X_2\right) < P_2 < -\left(\frac{X_1}{2} + X_2\right) \quad (2)$$

$$-\frac{X_2}{5} < P_3 < \frac{X_1 + X_2}{4} \quad (3)$$

where $X_1$ is the distance from the vertex of the lens surface of the first component $L_1$ which is adjacent to the eye to be examined to the vertex of the lens surface of the second component $L_2$ which is adjacent to the eye to be examined, $X_2$ is the combined center thickness of the second component $L_2$, the vertex of the lens surface of the second component $L_2$ which is adjacent to the observation aperture stop is the origin of the coordinates, the sign from the origin toward the eye to be examined is negative, $P_1$ is the distance to the first black point image position, $P_2$ is the distance to the second black point image position, $P_3$ is the distance to the third black point image position, and the direction of the observation aperture stop is positive.

Condition (1) which prescribes the position of the first black point image $P_1$ is a condition for efficiently eliminating the reflected light on the cemented surfaces in the first and second components. These cemented surfaces are indispensable for the correction of aberrations, particularly for the correction of chromatic aberration, and satisfying condition (1) is effective to eliminate the harmful reflected light created on these surfaces while accomplishing aberration correction well. As previously described, the position of the first black point image $P_1$ is a position substantially conjugate with the observation aperture stop with respect to the reflected light on each cemented surface, and the magnifications of the respective cemented surfaces with respect to the reflected light are substantially equal to each other. As the position of the first black point image $P_1$ moves toward the observation aperture stop, the radius of curvature of the second surface $r_2$ as the cemented surface of the first component $L_1$ becomes greater and the image magnification also becomes greater, while the radius of curvature of the fifth surface $r_5$ as the cemented surface of the second component $L_2$ becomes smaller and the image magnification also becomes smaller. Therefore, if the lower limit of condition (1) is departed from, the difference between the sizes of the images of the observation aperture stop by the respective surfaces will become excessively great and the black point images will become larger than necessary. If the position of the first black point image is moved in the opposite direction, namely, toward the eye to be examined, the tendency converse to what has been described above will become significant and again in this case, the black point images will become larger than necessary and the light beam necessary for observation and photographing will be substantially decreased. If within the range of condition (1), it will be possible to construct an objective lens in which the positions and magnifications of the images of the observation aperture stop by the cemented surfaces of the respective components can be made substantially coincident with each other and the difference in magnification is of the order of 1:0.7 at greatest and the first light-intercepting material hardly adversely affects the observing and photographing optical system and which is good in respect of aberrations.

Condition (2) which prescribes the position of the second black point image $P_2$ is closely associated with the radius of curvature of the convex surface of the first component which is adjacent to the observation aperture stop, i.e., the third surface. As the second black point image is moved toward the observation aperture stop, the radius of curvature of the third surface becomes smaller and the magnification of the image of the observation aperture stop with respect to the reflection on this surface also becomes smaller and this is preferable, but if the upper limit of condition (2) is exceeded, the refractive power of this surface will become excessively great and aberration correction will become difficult and also the lens aperture will become smaller, and this is disadvantageous for making the angle of view of the lens wide. Also, the working distance will become too short and this may prove a hindrance in practice. If conversely the second black point image is moved toward the eye to be examined, the radius of curvature of the third surface will become greater and the magnification of the image of the observation aperture stop with respect to the reflection on this surface will also become greater, and this leads to the necessity of making the second black point image larger than necessary. If the lower limit of condition (2) is departed from, the refractive power of this surface will become too small and making the angle of view of the lens wide will become difficult and aberration correction will also become difficult.

Condition (3) prescribes the position of the third black point image $P_3$ for eliminating the light reflected by the fourth surface as the convex surface of the second component. If the position of the third black point image is moved toward the observation aperture stop, the radius of curvature of the fourth surface will become greater, and this leads to the necessity of making the third black point image larger. If the upper limit of condition (3) is exceeded, the refractive power of the fourth surface will become smaller and the refractive power necessary for a wide angle of view will be deficient and therefore, not only making the angle of view wide will become difficult, but also the third black point image will become larger and the black point images will be formed near the position of the fundus of the eye to be examined and thus, the black points will become imaged at the center of the image of the eye fundus by the observing and photographing optical system. If conversely the third black point image is moved toward the eye to be examined, the radius of curvature of the fourth surface will become smaller and therefore, the size of the third light-intercepting material necessary for the formation of the third black point image will also become smaller, but if the lower limit of this condition is departed from, the radius of curvature will become too small and the refractive power will become excessively great, and not only aberration correction will become difficult, but also the working distance will become too short, and this is not practical.

In the construction of the embodiment shown in FIG. 1, the black point plate 4 having the fourth light-intercepting material $B_4$ is disposed between the relay lenses $L_7$ and $L_8$ in the illuminating system and this is projected into the objective lens by the relay lens $L_8$ to form the fourth black point image, whereas this fourth black point plate 4 is not for directly eliminating the light reflected by the lens surface of the objective lens, but for preventing part of the illuminating light diffracted by the edges of the first light-intercepting material $B_1$ and the third light-intercepting material $B_3$ present on the incident light side from the fourth light-intercepting material from forming annular stray light around the second light-intercepting material $B_2$.

For the convenience of description, the black point plates 1, 2, 3 and 4 have been shown as being separate from one another, but in order to facilitate the adjustment of the positions of these black point plates, it is of course possible to adhesively secure the black point plates to one another so that the thickness of each black point plate is equal to the on-axis spacing of the light-intercepting materials and construct the black point plates integrally with one another by enveloping the four light-intercepting materials in the black point plates.

Specific examples of the numerical values of the objective lens in the eye fundus observing and photographing optical system according to the present invention as described above will be shown in the table below. In the table, the numbers at the left end indicate the order from the eye to be examined, the refractive indices are values for d-line ($\lambda = 587.6$ nm), $d_0$ represents the distance between the cornea of the eye to be examined and the vertex of the first surface of the objective lens, and $d_6$ represents the distance between the vertex of the last surface of the objective lens and the observation aperture stop.

TABLE

| | Focal length f = 40.013 | Angle of view: 50° | |
| --- | --- | --- | --- |
| No. | Radius of curvature r | Center thickness of space d | Refractive index n |
| 1 | −42.966 | 0.9 | 1.71736 |
| 2 | 104.086 | 19.5 | 1.71300 |
| 3 | −35.454 | 3.5 | |
| 4 | *42.071 | 22.0 | 1.71300 |
| 5 | −57.293 | 0.9 | 1.58144 |
| 6 | 112.605 | | |

*Non-spherical surface
$d_0 = 42.966$
$d_6 = 112.605$
Black point image positions
(Projected positions of light-intercepting materials)
$P_1 = -13.95$
$P_2 = -46.0$
$P_3 = 0.61$ The conjugate magnifications of the observation aperture stop and its image by the reflection on the second surface $r_2$ and the fifth surface $r_5$ of the above-described objective lens are
$r_2$: −0.146
$r_5$: 0.118
respectively. (The negative value means the real image and the positive value means the virtual image.) As shown above, the absolute values of the magnifications of the reflected images on the respective surfaces are substantially coincident with each other. However, they are not completely coincident with each other, and the ratio of the magnifications is 1:0.81. As described above, it is preferable in eliminating the reflected light on the lens surface to make the two magnifications completely coincident with each other, but from the necessity of taking the balance with aberration correction and the total reflection on the lens surface into consideration, it is not always advisable in the overall performance of the lens system to make the two magnifications completely coincident with each other. Therefore, it is desirable that the ratio of the image magnifications of the second surface and the fifth surface be in the range of 1:1.5 to 1:0.7.

According to the present invention, as described above, an eye fundus observing and photographing apparatus can be realized in which the reflection conjugate positions of the observation aperture stop by the cemented surfaces of the first component adjacent to the eye to be examined and the second component adjacent to the observation aperture stop which constitute the objective lens are made coincident with each other and the conjugate magnifications thereof are also made coincident with each other, whereby for the elimination of the reflected light on these surfaces, it is only required to project a sufficiently small light-intercepting material which does not affect the observation and photographing light beam from a conjugate position in the illuminating system. Good aberration correction becomes possible by the cemented surfaces, and thus excellent imaging performance is provided.

What we claimed is:

1. An eye fundus observing and photographing apparatus having an illuminating optical system for supplying illuminating light to an eye to be examined, an optical system for observing and photographing the fundus of the eye to be examined through an observation aperture stop, and an objective lens common to said illuminating optical system and said observing and photographing optical system, said objective lens being comprised of a first component which is a positive meniscus lens having its concave surface facing the eye to be examined and a second component which is a positive meniscus lens having its concave surface facing said observation aperture stop, each of said first and second components being a cemented doublet comprised of a positive lens and a negative lens, said concave surface of said first component which is adjacent to the eye to be examined being formed so that the center of curvature thereof is coincident with a position conjugate with said observation aperture stop with respect to the entire objective lens, said concave surface of said second component which is adjacent to said observation aperture stop being formed so that the center of curvature thereof is coincident with the position of said observation aperture stop, said first component and said second component being formed so that a first position conjugate with said observation aperture stop with respect to reflected illuminating light on a cemented surface formed by the positive lens and the negative lens of said first component and a second position conjugate with said observation aperture stop with respect to reflected illuminating light on a cemented surface formed by the positive lens and the negative lens of said second component are substantially coincident with each other and said first component and said second component being formed so that the magnification of the images of said observation aperture stop by the reflection on said cemented surfaces of said first and second components are substantially equal to each other, first, second and third light-intercepting members being provided in said illuminating optical system, said first light-intercepting member being disposed so that the image thereof is substantially coincident with said first and second positions, said second light-intercepting member being disposed so that the image thereof is substantially coincident with a position conjugate with said observation aperture stop with respect to reflected illuminating light on the convex surface of said first component which is adjacent to said observation aperture stop, said third light-intercepting member being disposed so that the image thereof is substantially coincident with a position conjugate with said observation aperture stop with respect to reflected illuminating light on the convex surface of said second component which is adjacent to the eye to be examined.

2. An apparatus according to claim 1, wherein the positive lens of each of said first and said second components is a biconvex positive lens, the negative lens of each of said first and said second components is a biconcave negative lens, the positive lens and the negative lens of said first component are arranged in succession from the eye to be examined, the negative lens and the positive lens of said second component are arranged in succession from the eye to be examined, the image of said second light-intercepting member lies more adjacent to the eye to be examined than the image of said first light-intercepting member, and the image of said third light-intercepting member lies more adjacent to said observation aperture stop than the image of said first light-intercepting member.

3. An apparatus according to claim 2, satisfying the following conditions:

$$-\frac{2(X_1 + X_2)}{5} < P_1 < -\frac{X_1 + X_2}{5}$$

$$-\left(\frac{3X_1}{2} + X_2\right) < P_2 < -\frac{X_1}{2} + X_2$$

$$-\frac{X_2}{5} < P_3 < \frac{X_1 + X_2}{4}$$

where $X_1$ is the distance from the vertex of the lens surface of said first component which is adjacent to the eye to be examined to the vertex of the lens surface of said second component which is adjacent to the eye to be examined, $X_2$ is the combined center thickness of said second component, the vertex of the lens surface of said second component which is adjacent to the observation aperture stop is the origin of the coordinates, $P_1$ is the distance to the position of the image of said first light-intercepting member, $P_2$ is the distance to the position of the image of said second light-intercepting member, $P_3$ is the distance to the position of the image of said third light-intercepting member, and the direction of said observation aperture stop is positive.

4. An apparatus according to claim 2, wherein a fourth light-intercepting member for preventing said illuminating light diffracted by the edge of at least one of said first and third light-intercepting members from being transmitted to said objective lens is provided in said illuminating optical system.

5. An eye fundus observing and photographing apparatus having an illuminating optical system for supplying illuminating light to an eye to be examined, an optical system for observing and photographing the fundus of the eye to be examined through an observation aperture stop, and an objective lens common to said illuminating optical system and said observing and photographing optical system, said objective lens being comprised of a first component which is a positive meniscus lens having its concave surface facing the eye to be examined and a second component which is a positive meniscus lens having its concave surface facing said observation aperture stop, each of said first and second components being a cemented doublet comprised of a positive lens and a negative lens, said concave surface of said first component which is adjacent to the eye to be examined being formed so that the center of curvature thereof is coincident with a position conjugate with said observation aperture stop with respect to the entire objective lens, said concave surface of said second component which is adjacent to said observation aperture stop being formed so that the center of curvature thereof is coincident with the position of said observation aperture stop, said first component and said second component being formed so that a first position conjugate with said observation aperture stop with respect to reflected illuminating light on a cemented surface formed by the positive lens and the negative lens of said first component and a second position conjugate with said observation aperture stop with respect to reflected illuminating light on a cemented surface formed by the positive lens and the negative lens of said second component are substantially coincident with each other and said first component and said second component being formed so that the ratio of absolute values of the magnifications of the images of said observation aperture stop by the reflection on said cemented surfaces of said first and second components is in the range of 1:1.5 to 1:0.7, a light-intercepting member being provided in said illuminating optical system, said light-intercepting member being disposed so that the image thereof is substantially coincident with said first and second positions.

6. An apparatus according to claim 5, wherein another light-intercepting member is provided in said illuminating optical system, and said another light-intercepting member is disposed so that the image thereof is substantially coincident with a position conjugate with said observation aperture stop with respect to reflected illuminating light on the convex surface of said second component which is adjacent to the eye to be examined.

7. An apparatus according to claim 6, wherein a further light-intercepting member is provided in said illuminating optical system, and said further light-intercepting member is disposed so that the image thereof is substantially coincident with a position conjugate with said observation aperture stop with respect to reflected illuminating light on the convex surface of said first component which is adjacent to said observation aperture stop.

8. An apparatus according to claim 7, wherein the positive lens of each of said first and said second components is a biconvex positive lens, said negative lens of each of said first and said second components is a biconcave negative lens, the positive lens and the negative lens of said first component are arranged in succession from the eye to be examined, the negative lens and the positive lens of said second component are arranged in succession from the eye to be examined, the image of said further light-intercepting member lies more adjacent to the eye to be examined than the image of the first-mentioned light-intercepting member, and the image of said another light-intercepting member lies more adjacent to said observation aperture stop than the image of the first-mentioned light-intercepting member.

9. An apparatus according to claim 7, satisfying the following condition:

$$-\frac{2(X_1 + X_2)}{5} < P_1 < -\frac{X_1 + X_2}{5}$$

where $X_1$ is the distance from the vertex of the lens surface of said first component which is adjacent to the eye to be examined to the vertex of the lens surface of said second component which is adjacent to the eye to be examined, $X_2$ is the combined center thickness of said second component, the vertex of the lens surface of said second component which is adjacent to said observation aperture stop is the origin of the coordinates, $P_1$ is the distance to the position of the image of said light-intercepting member, and the direction of said observation aperture stop is positive.

10. An apparatus according to claim 7, satisfying the following condition $$-\left(\frac{3X_1}{2} + X_2\right) < P_2 < -\left(\frac{X_1}{2} + X_2\right)$$

where $X_1$ is the distance from the vertex of the lens surface of said first component which is adjacent to the eye to be examined to the vertex of the lens surface of said second component which is adjacent to the eye to be examined, $X_2$ is the combined center thickness of said second component, the vertex of the lens surface of said second component which is adjacent to said observation aperture stop is the origin of the coordinates, $P_2$ is the distance to the position of the image of said one of said two other light-intercepting members, and the direction of said observation aperture stop is positive.

11. An apparatus according to claim 7, satisfying the following condition:

$$-\frac{X_2}{5} < P_3 < \frac{X_1 + X_2}{4}$$

where $X_1$ is the distance from the vertex of the lens surface of said first component which is adjacent to the eye to be examined to the vertex of the lens surface of said second component which is adjacent to the eye to be examined, $X_2$ is the combined center thickness of said second component, the vertex of the lens surface of said second component which is adjacent to said observation aperture stop is the origin of the coordinates, $P_3$ is the distance to the position of the image of said other of said two other light-intercepting members, and the direction of said observation aperture stop is positive.

12. An apparatus according to claim 5, satisfying the following condition:

$$-\frac{2(X_1 + X_2)}{5} < P_1 < -\frac{X_1 + X_2}{5}$$

where $X_1$ is the distance from the vertex of the lens surface of said first component which is adjacent to the eye to be examined to the vertex of the lens surface of said second component which is adjacent to the eye to be examined, $X_2$ is the combined center thickness of said second component, the vertex of the lens surface of said second component which is adjacent to said observation aperture stop is the origin of the coordinates, $P_1$ is the distance to the position of the image of said light-intercepting member, and the direction of said observation aperture stop is positive.

* * * * *